Figure 1:
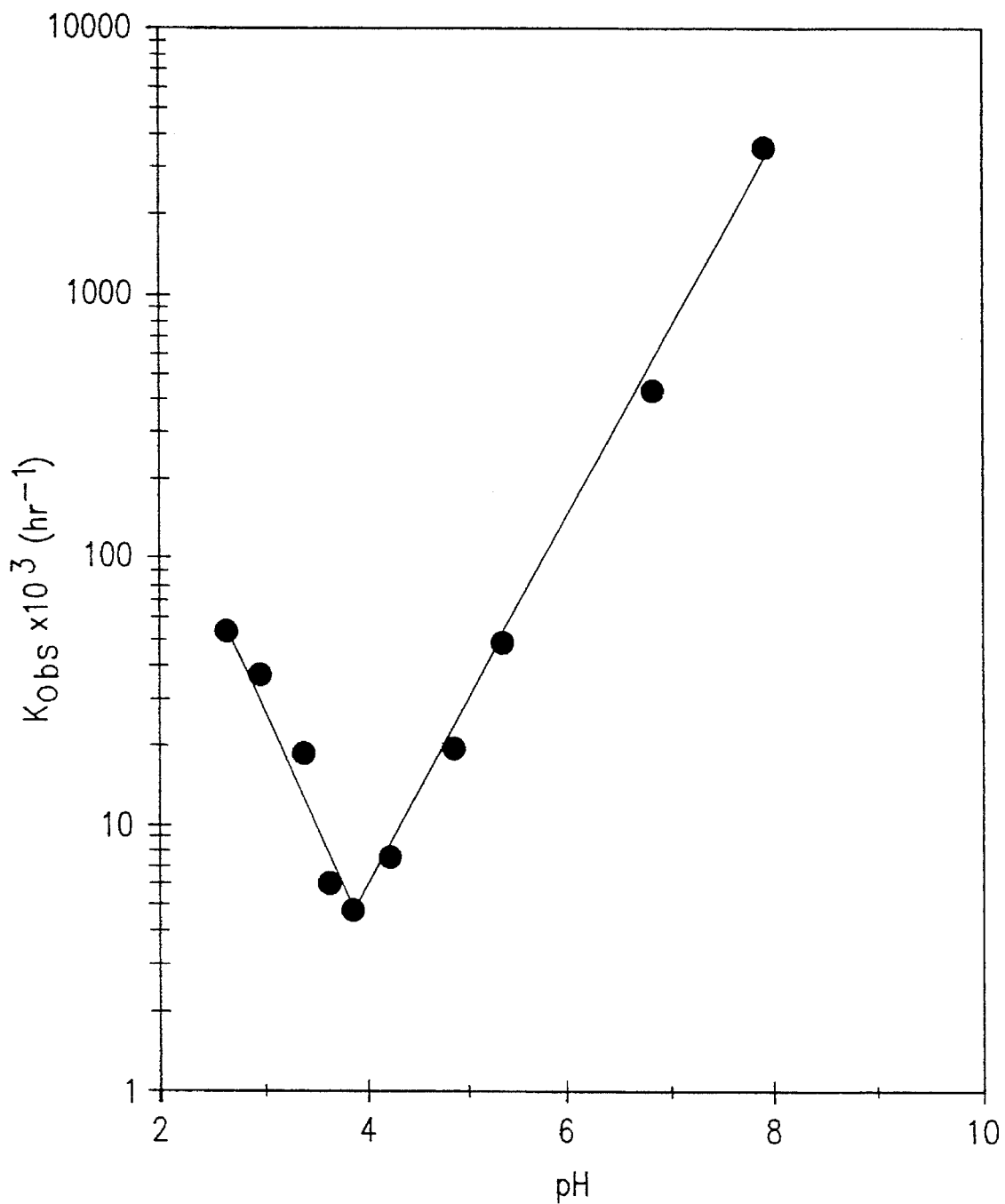

United States Patent [19]

Nassar et al.

[11] Patent Number: 5,508,268
[45] Date of Patent: Apr. 16, 1996

[54] PARENTERAL ELSAMITRUCIN FORMULATIONS

[75] Inventors: Munir N. Nassar, Manilus; Michael J. Reff, Syracuse; Sheeram N. Agharkar, Fayetteville, all of N.Y.

[73] Assignee: Bristol-Myers Squibb, New York, N.Y.

[21] Appl. No.: 105,541

[22] Filed: Aug. 12, 1993

[51] Int. Cl.$^6$ ........................................ A61K 31/71
[52] U.S. Cl. .................. 514/28; 536/4.1; 536/17.2; 536/18.7; 536/18.5
[58] Field of Search .................. 514/28; 536/4.1, 536/17.2, 18.5, 18.7

[56] References Cited

U.S. PATENT DOCUMENTS 4,518,589  5/1985  Konish et al. .................. 514/27
4,572,895  2/1986  Konish et al. .................. 435/75
4,873,261  10/1989  Miyazaki et al. .................. 514/462
4,963,356  10/1990  Calenoff et al. .................. 424/276.1

OTHER PUBLICATIONS

Investigational New Drugs, Schurig, et al., 7:175–8 (1989).
American Association of Pharmaceutical Scientists (AAPS) 5th Annual Mtg. Nov. 4–8, 1990.
"The Merck Index", 11th ed.; S. Budavari, editor; Merck and Co., Inc; 1989, p. 1358.

*Primary Examiner*—Douglas W. Robinson
*Assistant Examiner*—Kathleen Kahler Fonda
*Attorney, Agent, or Firm*—Sandra M. Nolan

[57] ABSTRACT

Stable parenteral antitumor formulations contain elsamitrucin salt, a stabilizer and a buffer. The formations are optionally stored in sealed containers under air or nitrogen headspace.

13 Claims, 3 Drawing Sheets

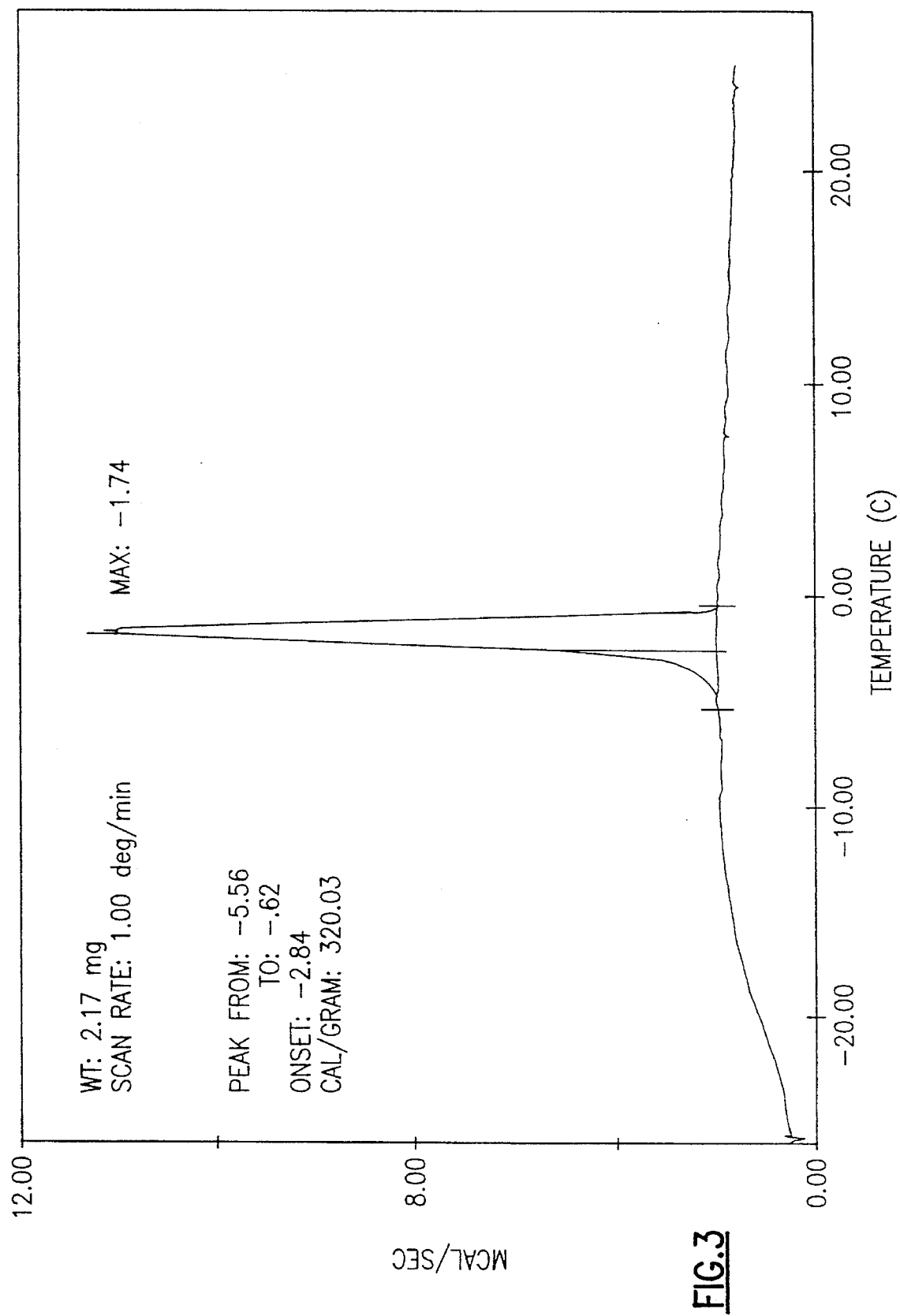

PARENTERAL ELSAMITRUCIN FORMULATIONS

BACKGROUND

Elsamitrucin is an antibiotic anticancer agent exhibiting in vitro cytotoxicity against murine and human tumor cell lines and in vivo antitumor activity against murine leukemias, murine solid tumors and human tumor xenografts.

Elsamitrucin's structure is:

[Chemical structure (I)]

Its preparation and properties are set out in U.S. Pat. Nos. 4,518,589 and 4,572,895. The disclosures of these documents are hereby incorporated herein by reference.

The drug is highly effective. However, its use in parenteral formulations is problematic because of its low solubility (<100 mcg/mL) in water and water/alcohol solutions. Attempts to solubilize the drug have led to the preparation of salts of same.

In *Investigational New Drugs*, 7:175–8 (1989), J. E. Schuring et al discussed the antitumor activity of elsamitrucin (also called "elsamicin" and "elsamicin A"). The in vitro and in vivo activity of the drug, as well as properties of its lactate and succinate salts are disclosed.

Lyophilized 1:1 elsamitrucin succinate was described at the American Association of Pharmaceutical Scientists (AAPS), 5th Annual Meeting, Nov. 4–8, 1990. The salt was in a solid lyophilized formulation containing mannitol as a bulking agent. The solid is reconstituted with Sterile Water for Injection prior to use. The resultant solutions are stable for 48 hours at 25° C.

In a preferred embodiment, a stable ready-to-use formulation is provided. It contains a 1:1 elsamitrucin: succinic acid in-situ salt solution(5 mg elsamitrucin base/mL) in water, with pH adjustment to 4 using hydrochloric acid and 0.1% acetone sodium bisulfite stabilizer. In a highly preferred embodiment, the solution is purged with nitrogen ($N_2$) and the headspace gas is $N_2$. This solution has a projected shelf life of at least 18 months at about 15° C. to about 30° C.

Advantages

The solutions of the invention have several advantages over those of the prior art. They are liquid, so that they can be used as is or they can be diluted with one or more carrier(s).

Depending upon the stabilizer employed, the solutions retain up to 96% potency after 3 months at 50° C. Their controlled room temperature (15° C.–30° C.) stability is even greater.

These and other advantages of the invention will be better understood after consideration of the following drawings, specification and claims.

DESCRIPTION OF THE INVENTION

Unless stated otherwise, all percentages recited herein are weight percentages, based upon total composition weight.

DRAWINGS

FIG. 1 is a plot of the pH-rate profile for the degradation of elsamitrucin base in aqueous buffers at 50° C. It shows the rate of degradation of elsamitrucin base as a function of pH. This plot shows the pH at which elsamitrucin is most stable in solution.

Figure 2:
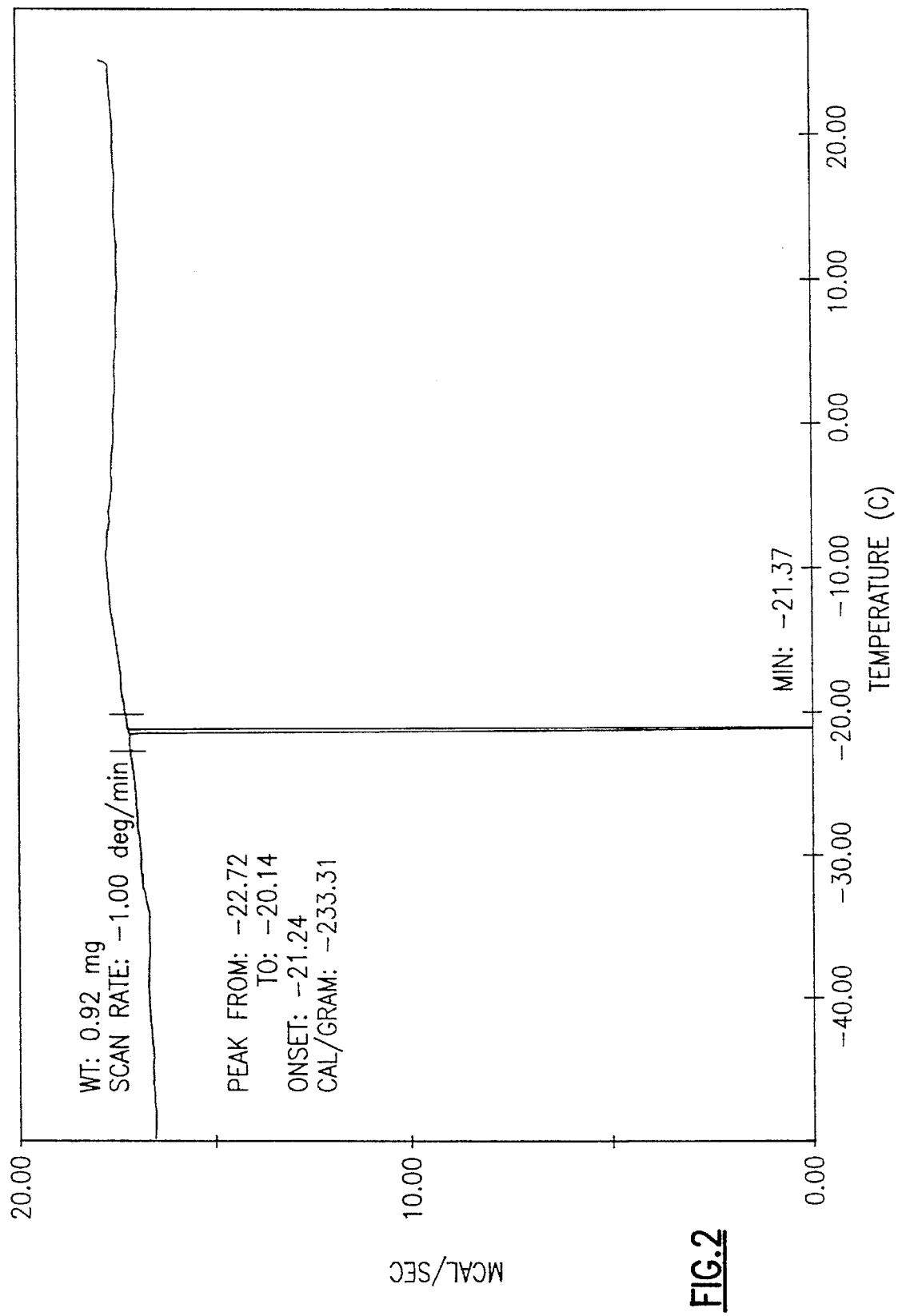

FIG. 2 is a Differential Scanning Calorimetry thermogram (cooling curve) for the elsamitrucin: succinic acid in-situ salt solution containing mannitol. This thermogram is performed on the solution prior to lyophilization to determine the thermal characteristics of the solution. It demonstrates a sharp exothermic transition having an onset of about −21° C., which is the equilibrium freezing temperature that is needed to develop a lyophilization cycle.

FIG. 3 is the Differential Scanning Calorimetry thermogram, warming curve, for the same solution used to determine the cooling curve (FIG. 2). It shows a broad endotherm with an onset of about −3° C, probably due to the melting of ice. No true eutectic temperature was detected on warming the frozen solution.

Elsamitrucin

The base compound elsamitrucin is derived from the fermentation of a non-Streptomyces actinomycete strain (J907-21). A biologically pure culture of the strain has been prepared by conventional procedures and deposited with the American Type Culture Collection in Rockville, Md. under Accession Code ATCC-39417. The deposit was made in accordance with applicable law before the issuance of U.S. Pat. No. 4,518,589, which patent describes the preparation and characteristics of elsamitrucin.

Analytical studies with bulk elsamitrucin revealed the presence of about 2–6% residual solvents. e.g., methanol, ethanol, chloroform, n-butanol and t-butanol. An elsamitrucin succinate in situ salt solution (1:1 mole) containing 2.5 mg/mL drug base and 25 mg/mL mannitol was prepared. The solution was filtered through a 0.2 micron Millipore GV filter and 2 mL aliquots were filled into 6 cc flint glass vials and lyophilized. The samples were analyzed by GLC to quantify residual solvent levels.

Useful conditions for lyophilization include:

The vials are placed in the lyophilizer with the shelves precooled to a temperature of 4° C.±2° C. When the product temperature reaches 4° C., the shelf temperature is set at −35° C. and the product allowed to freeze for 2 hours after the product temperature reaches −30° C. The condenser is then switched on and cooled to −60° C.±3° C. Vacuum of 150±50 microns is then applied. Primary drying is performed at a shelf temperature of −25° C.±3° C. for 24 hours after which the shelf temperature is raised to 25° C. Secondary drying is performed at a shelf temperature of 25° C. for 4 hours.

The device used for the lyophilization was a Virtis Unitop 200 lyophilizer, the Virtis Company, Gardiner, N.Y.

Elsamitrucin Salts

Salts of elsamitrucin were prepared using a variety of acids. Useful organic and inorganic acids include: hydrochloric, L(+)-lactic, L-tartaric, D-glucuronic, methane sulfonic, adipic, and succinic. Succinic acid salts are preferred.

The molar ratio of elsamitrucin in the acid salt should be from about 1:1 to about 1:2. Thus, the 1:1 and 1:2 elsamitrucin:succinic acid salts (i.e., elsamitrucin succinates) are preferred.

The salts will be present in the formulations in amounts from about 1 mg/mL to about 10 mg/mL, preferably about 2 mg/mL to about 8 mg/mL. These formulations may be diluted, so that lower drug concentrations result.

Buffers

The optimum pH of the solutions of the invention has been found to be about 3.5 to about 4.5, with a pH of about 4.0 being highly preferred.

The buffering agent selected to bring the elsamitrucin salt solutions to the desired pH will generally be acid. While any acid which does not adversely affect the effectiveness of the drug formulations may be employed, it is generally preferred that hydrochloric, succinic, L(+)-lactic or L-tartaric acid be used. Hydrochloric acid is highly preferred.

Stabilizers

The parenteral compositions of the invention will preferably contain at least one antioxidant. However, antioxidant use, while preferred, is not essential.

The stabilizer employed is generally a sulfur- and alkali metal-containing antioxidant. Useful stabilizers include sodium metabisulfite, acetone sodium bisulfite and sodium formaldehyde sulfoxylate. Acetone sodium bisulfite is highly preferred.

When employed, the antioxidant will be present in stabilizing amounts, generally from about 0.01% to 1%, with from about 0.05% to 0.1% being preferred.

Headspace/Purge Gas

The solutions of the invention are stored in sealed containers—preferably glass vials—having headspaces of air or an inert gas. In preferred embodiments, the headspace gas is nitrogen ($N_2$).

Optionally, the solutions are purged—i.e., by bubbling gas through at room, or slightly higher, temperature—to remove gaseous impurities and reduce the amount of residual oxygen therein. While the solutions may be purged with air, it is highly preferred that they be purged with nitrogen gas.

In preferred embodiments, both the purging gas and the headspace gas will be air or nitrogen, with nitrogen highly preferred.

Carrier(s)

Suitable amounts of conventional pharmaceutically acceptable carriers can be employed. Water is the preferred carrier for the formulations of the invention. However, up to 50 volume % of the water used may be replaced with 0.9% sodium chloride solution or other carrier(s).

The amount of water and/or other carrier(s) used will range from about 0.5% to about 99.5%. The amount of carrier employed depends on whether the formulation is to be used as is or is to be diluted before administration.

Dilution

When the solutions of the invention are to be diluted, that dilution, or reconstitution, should be effected using Sterile Water for Injection or Dextrose 5% in water ($D_5W$). Sterile water is preferred.

When used, diluents can be present in various quantities. The use of from 10 to 99.5% of additional diluents is contemplated.

Other ingredients

The formulations of the invention may contain a variety of excipients conventionally employed in pharmaceutical preparations, particularly parenteral ones. Thus, surfactants, antimicrobial preservatives and the like may be used in suitable quantities.

Generally, such ingredients will be used in amounts of about 0.1 to about 10%.

EXAMPLES

The following tables illustrate the solution stability of elsamitrucin solutions containing either 1:1 or 1:2 elsamitrucin:succinic acid salts and various other ingredients/parameters as indicated.

The solutions were prepared using the following general procedure:

Elsamitrucin powder (0.3157 g) was weighed into a pre-calibrated 100 mL Type I glass vial. Succinic acid (0.0548 g) was weighed and placed in the same vial. Approximately 30 mL of Sterile Water for Injection was then added and the solution stirred for about 15 minutes. The pH of the solution was measured and found to be 4.38. Two millileters of 0.1N hydrochloric acid was added to achieve a pH of 4. Sodium metabisulfie and/or acetone sodium bisulfite 60 mg (0.1%) was then added. The solution was brought up to volume (60 mL) with Sterile Water for Injection and stirred for approximately 30 minutes. The solution was filtered using a Millex GV filter, 0.2 micron. The filtered solution was then filled into 3 cc vials (2 mL fill volume), sealed and placed at various stability stations.

In all cases, the solution contains the equivalent of 5 mg/mL of elsamitrucin base. All solutions have been adjusted to pH 4 with HCl.

TABLE 1

Solution Stability of 1:1 Elsamitrucin Succinate salt in Ready to Use Formulations at Various Temperatures (Air Headspace Gas)

| STORAGE CONDITIONS | | | |
|---|---|---|---|
| TEMP (°C.) | TIME (MONS) | ELSAMITRUCIN PERCENT REMAINING | pH |
| | INITIAL | 100.0 | 4.00 |
| 30 | 6 | 94.7 | 4.16 |
| | 9 | 92.1 | 3.93 |
| | 12 | 90.4 | 4.07 |
| 40 | 6 | 87.1 | 3.96 |
| | 12 | 64.9 | 3.77 |
| 50 | 1 | 94.6 | — |
| | 2 | 81.9 | 3.89 |
| | 3 | 74.7 | — |

TABLE 2

Solution Stability of Elsamitrucin Formulations containing 1:2 Elsamitrucin Succinate Salt at Various Temperatures (Air Headspace Gas)

| STORAGE CONDITIONS | | | |
|---|---|---|---|
| TEMP (°C.) | TIME (MONS) | ELSAMITRUCIN PERCENT REMAINING | pH |
| | INITIAL | 100.0 | 4.00 |
| 30 | 3 | 91.9 | 4.03 |
| | 9 | 83.4 | 3.98 |
| 40 | 6 | 74.1 | 3.92 |
| 50 | 1 | 88.9 | 3.88 |
| | 2 | 75.3 | 3.83 |

TABLE 2-continued

Solution Stability of Elsamitrucin Formulations containing 1:2 Elsamitrucin Succinate Salt at Various Temperatures (Air Headspace Gas)

| STORAGE CONDITIONS | | | |
|---|---|---|---|
| TEMP (°C.) | TIME (MONS) | ELSAMITRUCIN PERCENT REMAINING | pH |
| | 3 | 63.9 | 3.88 |

TABLE 3

Solution Stability of Elsamitrucin Formulations containing 1:1 Elsamitrucin Succinate Salt at Various Temperatures (Air Headspace Gas)

| STORAGE CONDITIONS | | | |
|---|---|---|---|
| TEMP (°C.) | TIME (MONS) | ELSAMITRUCIN PERCENT REMAINING | pH |
| | INITIAL | 100.0 | 4.00 |
| 30 | 6 | 98.1 | 4.15 |
| | 9 | 100.0 | 3.92 |
| | 12 | 96.2 | 4.19 |
| 40 | 6 | 94.4 | 4.04 |
| | 12 | 90.4 | 4.21 |
| 50 | 1 | 93.2 | — |
| | 2 | 90.4 | 4.00 |
| | 3 | — | — |

TABLE 4

Solution Stability of Elsamitrucin Formulations containing 1:1 Elsamitrucin Succinate Salt and Sodium Metabisulfite at Various Temperatures*

| STORAGE CONDITIONS | | | |
|---|---|---|---|
| TEMP (°C.) | TIME (MONS) | ELSAMITRUCIN PERCENT REMAINING | pH |
| | INITIAL | 100.0 | 4.00 |
| 30 | 3 | 106.5 | 3.83 |
| | 6 | 104.7 | 3.66 |
| | 12 | 99.5 | 3.79 |
| 40 | 6 | 106.3 | 3.93 |
| | 12 | 96.0 | 4.07 |
| 50 | 1 | 103.1 | 3.83 |
| | 2 | 101.4 | 3.75 |
| | 3 | 96.6 | 3.45 |

*0.1% sodium metabisulfite; nitrogen headspace gas.

TABLE 5

Solution Stability of Elsamitrucin Formulations containing 1:1 Elsamitrucin Succinate Salt and Acetone Sodium Bisulfite at various Temperatures*

| STORAGE CONDITIONS | | | |
|---|---|---|---|
| TEMP (°C.) | TIME (MONS) | ELSAMITRUCIN PERCENT REMAINING | pH |
| | INITIAL | 100.0 | 4.00 |
| 30 | 6 | 101.3 | 3.88 |
| | 12 | 97.9 | 3.89 |
| 40 | 6 | 106.3 | 3.93 |

TABLE 5-continued

Solution Stability of Elsamitrucin Formulations containing 1:1 Elsamitrucin Succinate Salt and Acetone Sodium Bisulfite at various Temperatures*

| STORAGE CONDITIONS | | | |
|---|---|---|---|
| TEMP (°C.) | TIME (MONS) | ELSAMITRUCIN PERCENT REMAINING | pH |
| | 12 | 83.3 | 3.20 |
| 50 | 1 | 100.3 | 3.75 |
| | 2 | 100.1 | 3.47 |
| | 3 | 95.8 | 3.68 |

*0.1% acetone sodium bisulfite; nitrogen headspace gas.

TABLE 6

Solution stability of Elsamitrucin Formulations containing Sodium Formaldehyde Sulfoxylate at Various Temperatures*

| STORAGE CONDITIONS | | | |
|---|---|---|---|
| TEMP (°C.) | TIME (MONS) | ELSAMITRUCIN PERCENT REMAINING | pH |
| | INITIAL | 100.0 | 4.00 |
| 30 | 6 | 80.9 | 3.92 |
| 50 | 1 | 70.3 | 3.82 |
| | 3 | 68.9 | 4.11 |

*0.1% sodium formaldehyde sulfoxylate; nitrogen headspace gas.

Reasonable variations, such as those which would occur to a skilled artisan, can be made herein without departing from the scope of the invention.

We claim:

1. An oxidatively stable composition consisting essentially of a solution of:

(a) an acid salt of elsamitrucin;

(b) a stabilizing amount of an antioxidant;

(c) sufficient buffer to maintain a solution pH of about 3.5 to about 4.5; and (d) a pharmaceutically acceptable carrier.

2. The composition of claim 1 wherein the acid is at least one selected from the group consisting of: hydrochloric, lactic, tartaric, glucuronic, methanesulfonic, adipic and succinic.

3. The composition of claim 2 wherein the molar ratio of drug base to acid is from about 1:1 to about 1:2.

4. The composition of claim 3 wherein the salt is an elsamitrucin:succinic acid salt.

5. The composition of claim 1 wherein the antioxidant is at least one selected from the group consisting of: sodium metabisulfite, acetone sodium bisulfite and sodium formaldehyde sulfoxylate.

6. The composition of claim 5 wherein the antioxidant is acetone sodium bisulfite.

7. The composition of claim 1 wherein the pH is about 4.

8. The composition of claim 7 wherein the salt is a 1:1 elsamitrucin:succinic acid salt.

9. The composition of claim 8 wherein the antioxidant is acetone sodium bisulfite.

10. A process for stabilizing elsamitrucin against oxidation comprising the steps:

(1) preparing an acid salt of elsamitrucin:

(2) dissolving the salt in a carrier;

(3) adjusting the pH of the resultant solution to about 3.5 to about 4.5 with a buffer; and (4) admixing a stabilizing amount of an antioxidant with the buffered solution.

11. The process of claim 10 which includes the additional step of: maintaining the buffered solution under nitrogen headspace.

12. The process of claim 10 which includes the additional steps of:

(5) purging the buffered solution with nitrogen gas; and (6) maintaining the purged solution under nitrogen headspace.

13. A product useful for the parenteral treatment of tumors comprising a sealed container which contains:

(i) a pH 3.5 to 4.5 solution of an elsamitrucin salt in admixture with an antioxidant, and (ii) nitrogen headspace gas.

\* \* \* \* \*